United States Patent [19]

Suzuki et al.

[11] Patent Number: 5,602,304
[45] Date of Patent: Feb. 11, 1997

[54] HAIRLESS MOUSE

[75] Inventors: Hiroshi Suzuki, Urawa; Keigo Yorozu, Kamiina-gun, both of Japan

[73] Assignee: Chugai Seiyaku Kabushiki Kaisha, Tokyo, Japan

[21] Appl. No.: 197,619

[22] Filed: Feb. 18, 1994

Related U.S. Application Data

[63] Continuation of Ser. No. 875,407, Apr. 29, 1992, abandoned.

[30] Foreign Application Priority Data

Apr. 30, 1991 [JP] Japan ................................. 3-099088

[51] Int. Cl.$^6$ .............................. C12N 5/00; A61K 49/00
[52] U.S. Cl. ................. 800/2; 800/DIG. 3; 800/DIG. 4; 800/DIG. 5; 424/9.2
[58] Field of Search .................................. 800/2, DIG. 3, 800/DIG. 4, DIG. 5; 424/9

[56] References Cited

PUBLICATIONS

Tenenhouse et al. (1974) Nature 251, 431–432.
Agin et al (1983) Photochem. Photobiol. 37, 559–564.
*Jpn. J. Zootech.*, vol. 56, No. 2, pp. 931–937 (1985) (English Summary).
*Domestic Animal Breading Journal*, vol. 16, No. 4, pp. 147–151 (1971) (English Summary).
*J. Heredity*, pp. 173–174.
*J. Heredity*, pp. 45–46 (1951).
*Jap. J. Genetics*, vol. 47, No. 4, pp. 297–299 (1972).
*J. Heredity*, pp. 151–154 (1953).
*J. Heredity*, pp. 467–470.
*J. Heredity*, pp. 297–300.
*Genet. Res. Camb.*, vol. 8, Part 3, pp. 295–309 (1966).
*Medicine and Biology*, vol. 75, No. 1, pp. 28–31 (1967).
*Science*, vol. 148, pp. 1471–1473 (1965).

*Primary Examiner*—Deborah Crouch
*Attorney, Agent, or Firm*—Foley & Lardner

[57] ABSTRACT

The DEC strain of mouse which inherits by a dominant gene the following properties;

(1) the mouse suffers from alopecia when 6 to 7 weeks old;

(2) the alopecia gradually progresses, and over about 5 months a hairless condition is reached, as observed by the naked eye;

(3) at 12 to 13 weeks old, the eyeballs of all suffering individuals project; and (4) melanin pigment is deposited in the epidermal base layer and corium connective tissue.

2 Claims, 2 Drawing Sheets

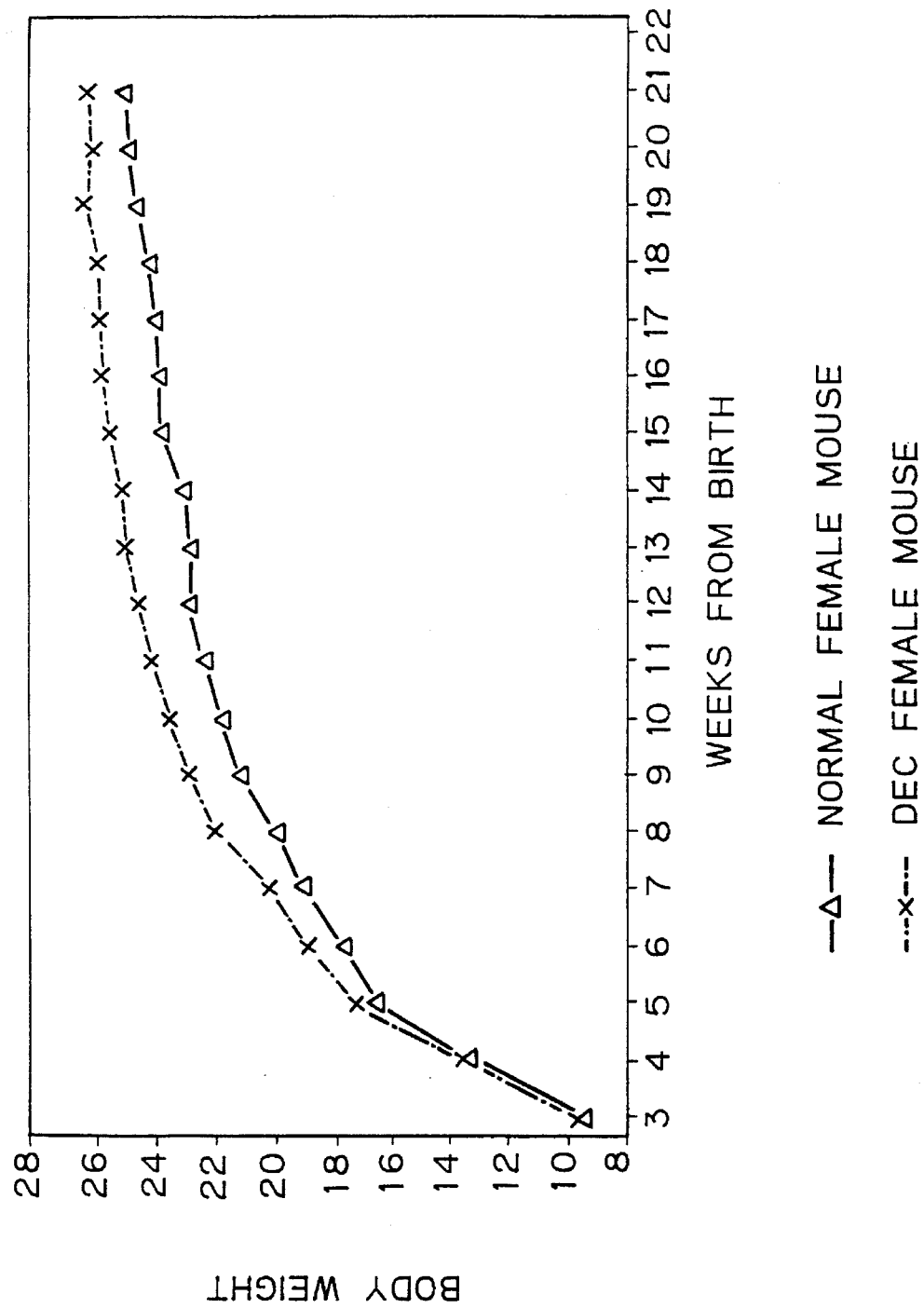

HAIRLESS MOUSE

This application is a continuation of U.S. application Ser. No. 07/875,407 filed Apr. 29, 1992 abandoned.

BACKGROUND OF THE INVENTION

1. Field of the Invention

The present invention relates to a novel strain of an animal. The present animal is an experimental mouse, which is suffering or will suffer from alopecia, has a small number of hair follicles, and has a deposition of melanin pigment in the epidermal basal layer and in the corium connective tissue. These phenotypes are inherited by an autosomal dominant gene. Due to these characteristics, the present mouse is very useful in the field of dermatology, especially as an animal model for human disease or an experimental animal in studies of alopecia, photodermatosis, and further, as an experimental animal for studies of transdermal absorption in the drug metabolism field. Accordingly, the present invention is useful in the medical field, including pharmacology, for studies of the pathogenesis and therapy of human alopecia and photodermatosis, and for studies of transdermal drug absorption.

2. Description of the Related Art

As mice exhibiting hereditary hypotrichosis, atrichosis or alopecia in the entire hair covering thereof, there are known hairless (H. C. Brooke. Hairless mice. J. Hered. 17,173–174 (1926.); rhino (A. Howard. "Rhino", an allele of hairless in the house mouse. J. Hered. 31, 467–470 (1940).); ichthyosis (T. C. Cater and R. S. Phillips. Ichthyosis, a new recessive mutant in the house mouse. J.Hered. 41, 297–300 (1950).); bald (E. D. Garber. "Bald", a second allele of hairless in the house mouse. J. Hered. 43, 45–46 (1952).); ragged (T. C. Cater and R. J. S. Phillips. Ragged, a semidominant coat texture mutant. J. Hered. 45, 151–154 (1954).); asebia (A. H. Gates and M. Karasek. Hereditary absence of sebaceous glands in the mouse, Science 148, 1471–1473 (1965).); nude (S. P. Flanagan. 'Nude', a new hairless gene with pleiotropic effects on the mouse. Genet. Res., Camb. 8, 295–309 (1966).); naked (H. Muto, developmental changes of epidermal cells of naked mouse, Igaku to Seibutsugaku (Medicine and Biology) 75, 28–31 (1967).); and glabrous (S. Tsujii and H. Matsushita. "Glabrous" a new hair deficient mutant in the house mouse. Jpn. J. Genetics 47, 297–299(1972).) Almost all of the above, however, are governed by a recessive inheritance, and therefore, are basically different from the present mouse.

Only the naked mouse is reported to be governed by a dominant gene, but this mouse is clearly different from the present mouse in that the reported naked mouse can be distinguished from a normal individual at 10 weeks old, a cornification of the skin in the naked mouse is remarkable, and this cornification causes alopecia. Known mice having alopecia are listed in Table 1.

TABLE 1

List of reports on mice exhibiting hereditary hypotrichosis, atrichosis, hairless or alopecia No. 1

| Name | Genetic type (gene) | Type of alopecia, and characteristics of hair and skin | Other characteristics | Author |
|---|---|---|---|---|
| hairless | Recessive (hr) | When about six weeks old, grew a short coat, looking as if it had been singed, which disappeared in a few days. | Bad in Nursing and vibrissae is normal | Brooke (1926) |
| rhino | Recessive ($hr^{rh}$) | Epilation occurs from 2 weeks old, entire epilation except for vibrissae from about 50 days old. The skin forms remarkable wrinkles as time elapses, a large number of cysts are formed. No cyclic regrowth of tylotrichs. | Elongation of the claws and reduced mammary gland tissue. | Howard (1940) |
| ichthyosis | Recessive (ic) | The skin dries hardens and becomes scaly. Dosal guard hair are still scarcely visible at 6 days old. An older mouse often grows a thin, curly coat. | Vibrissae are short and heavily curled. | Cater et al. (1950) |
| bald | Recessive (ba) | Hairs were normal in appearance until the 16th day when the hair just above the eyes and around the nose started to fall out, and usually completely bald within 22–28 days. | Vibrissae are lost after 28–30 days but shorter, curved vibrissae may sometimes appear after several weeks. | Garben (1952) |
| ragged | Semidominant (Ra) | Homo: Adults are naked, their few isolated pelage hairs being confined to the posterior and ventral part of the body. Sinus hair are few and short. Hetero: Distinguished from normal individuals by 9 days old. The coat of adult looks sparse and lacks cohesion. Many guard hairs are present. Proportion of zigzags is much lower than in normal mice. | The ears and fail are pigmented. Most of homozygotes die shortly. The distribution of the yellow agouti pattern is abnormal. | Cater et al. (1953) |
| asebia | Recessive (ab) | Distinguished from normal individuals when 7–9 days old. Alopecia increase until adulthood. Lack of sebaceous gland. The base of follicle sometimes exhibits excessive development, but hair production is faulty. Pruritus (inflammation with itching) occurs around eyes in old-age. Hyperkeratosis. | Delay of growth. | Cates et al. (1965) |
| nude | Recessive (nu) | Growth of a first coat is inhibited. | | Flanagan (1966) |
| naked | Dominant (N) | Distinguished from normal individuals on the day 10 after bith (because of poor hair in parts other than lumbar and tail). Hyperkeratosis of skin is remarkable, and epilation caused thereby. Hair root cells are relatively normal. | | Muto (1972) |
| glabrous | Recessive (gs) | Failure of a normal juvenile hair growth. Abnormalities in for development are readily detectable by the fifth of sixth day after birth, Hyperkeratosis. Monotrich, zigzag is not present. | Twisted and crooked vibrissae. Complete absence of sebaceous glands. Smaller in size than their normal litter mates at birth. | Tsujii et al. (1972) |

Most mice reported to exhibit a hypotrichosis an atrichosis, an alopecia or a hairless, in hereditary, are epilated soon after birth, the epilation rapidly progresses, the cornification of the skin is accelerated, and a remarkable number of wrinkles is formed.

Although as an animal model for alopecia and photodermatosis of human, mice not exhibiting an extreme hypertrophy of the skin and not accelerating cornification are preferred but mice satisfying these requirements have not been found. Moreover, since a mouse does not have melanocyte in the epidermis and has many hair follicles, it is not suitable as an animal model for a human for experiments of an induction of photodermatosis or for transdermal absorption experiments.

Although mice are widely used as the most useful experimental animals in the medical and pharmacological research fields, and many animal models for human diseases have been developed, in the field of alopecia, a mouse model acceptable for practical use has not yet been developed.

Therefore, the present invention is intended to provide a decalvant mouse suitable as an alopecia model for a human and not having the above-mentioned drawbacks. To obtain suitable model animals, the present inventors found a mutant mouse and carried out a breeding and tests of characteristics, and as a result, succeeded in the breeding of a novel strain of mouse.

SUMMARY OF THE INVENTION

Accordingly, the present invention provides a novel strain of mouse which inherits by a dominant gene the following properties:

(1) the mouse suffers from alopecia when 6 to 7 weeks old;

(2) the alopecia gradually progresses, and over about 5 months, a hairless condition is reached and can be observed by the naked eye;

(3) at 12 to 13 weeks old, the eyeballs of all suffering individuals project; and (4) melanin pigment is deposited in the epidermal basal layer and corium connective tissue.

DESCRIPTION OF THE PREFERRED EMBODIMENT

Finding and breeding the animal

Figure 1:
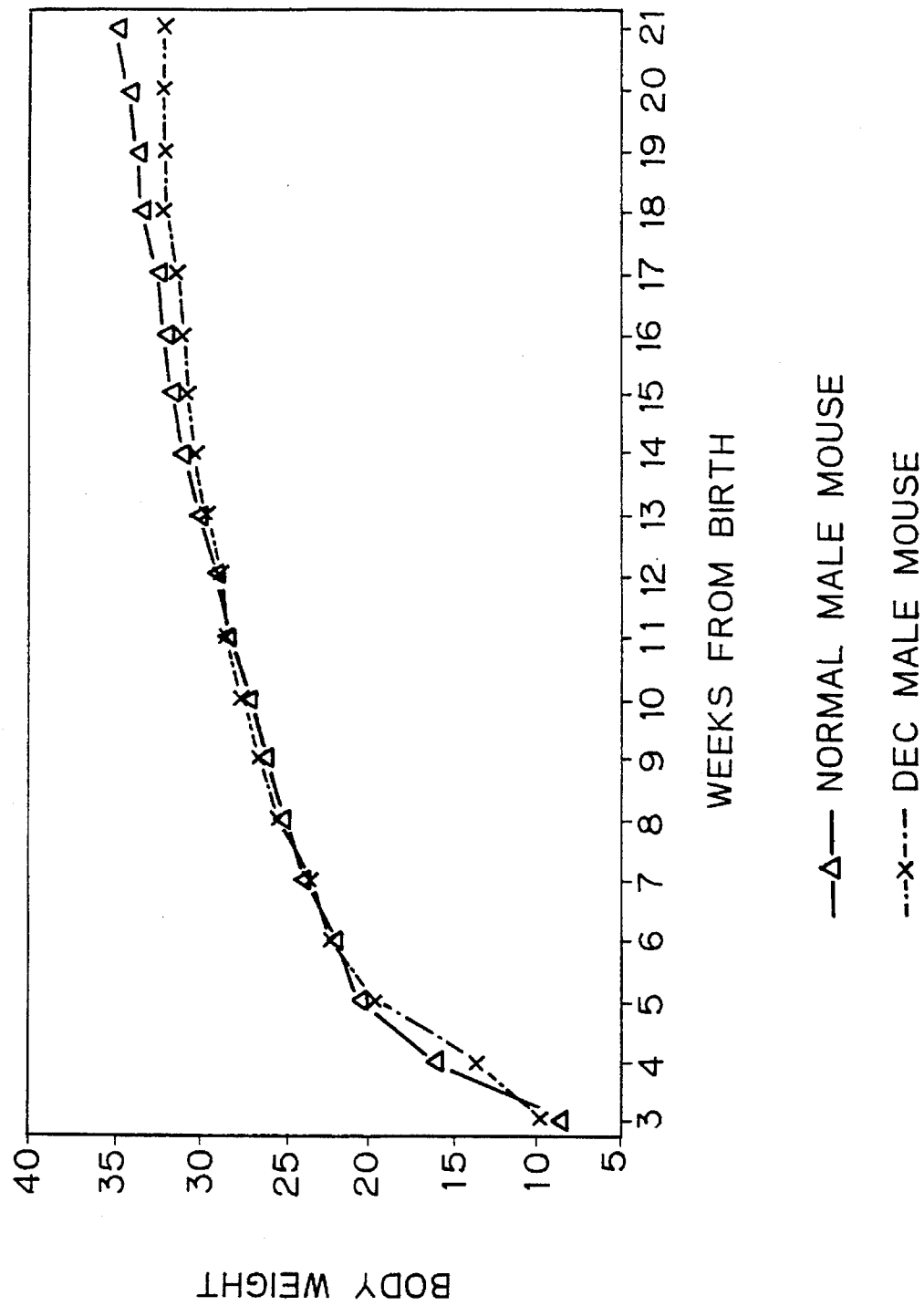
FIG. 1 represents a growth curve of a male decalvant mouse of the present invention, in comparison with that of a normal male mouse; and, FIG. 2 represents a growth curve of a female decalvant mouse of the present invention, in comparison with that of a normal female mouse.

The present animal was originally found during the production of a transgenic mouse by introducing a rat growth hormone gene into (C57BL×C3H)FI fertilized egg. After weaning of the young animal, a female mouse exhibiting systemic epilation was found. This mouse was then crossed with a normal C57BL/6J mouse, to obtain 39 young mice by 5 deliveries. Among the obtained mice, 13 animals (33%) suffered from systemic alopecia, like the female parent.

Nevertheless, the degree of epilation deviates individual by individual, and the decalvant mice were classified into three groups, i.e., ±, +, and ++, according to the density of hair on the dorsal skin thereof. The group of mice in which epilation progresses to the greatest extent reached a complete epilation (hairless) condition except for the face, and a density of hair of $57.5 \pm 50.5/cm^2$ was observed under a stereomicroscope (++).

For mice having a moderate symptom of alopecia (+), although the presence of hair was observed by the naked eye, the hair did not provide an entire coverage, the entire surface of the skin could be observed, and the density of hair was $252.5 \pm 136.8/cm^2$. Regarding mice having the lightest symptom of alopecia (±), although hair covered the entire skin, since the distribution of hair was rough and the gross is apparently lost, it was easy to distinguish these mice from a normal mouse. A density of hair of $4700 \pm 1003/cm^3$, was observed under a stereomicroscope. Note, a density of hair of normal individuals is $7750 \pm 1255/cm^2$. Normal individuals and individuals having ± alopecia had more than one hair per hair follicle, and individuals having + or ++ alopecia had only one hair per hair follicle.

Alopecia progresses gradually and the epilation starts when at an age of 6 to 7 weeks, and takes about 5 months to reach a hairless condition as observed by the naked eye.

For the F2 generation obtained by a brother-to-sister mating of suffering individuals, a ratio of alopecia individuals:normal individuals was 134:41 (female 77:22; male 57:17), and therefore, it was assumed that the trait of alopecia is inherited by an autosomal dominant gene. Although it is not clear whether the mouse of the present invention was generated as a result of an insertional mutation with a rat growth hormone gene, or because of a spontaneous mutation, the gene governing the trait of alopecia is tentatively designated as a "dec" gene.

The F3 generation and subsequent generations were bred by a brother-to-sister mating of suffering individuals, similar to the F2 breeding, and it was confirmed that the trait of alopecia is inherited according to Mendel's law.

Breeding and reproduction of the present animal

Breeding and reproduction of the present animal can be carried out according to a conventional brother-to-sister mating.

A pair of female and male animals, which are about 8 weeks old, are constantly kept in a single cage to allow mating, delivery and nursing. The number of new born animals per one parturition is 6.9 in average, and almost 100% of the new born animals reach weaning. A female mouse can bear several times in her life, the reproduction efficiency of the present animal is very high, and therefore, only a small number of pairs of animals are sufficient to maintain the strain.

Note, more than ten pairs of the present animal are constantly kept in CHUGAI SEIYAKU KABUSHIKI KAISHA, and about 300 embryos have been frozen and can be furnished. Moreover, the embryos were deposited with the American Type Culture Collection (ATCC) as ATCC 72004 on Apr. 9, 1991.

Production of the animal

Animals of the present invention can be produced by brother-to-sister mating, which is a conventional method for reproduction of inbred animals. For example, 5 pairs of parents provide 35 (=5×6.9) new born animals through one birth, and a next generation may provide 120 (35÷2×6.9) new born animals. These animals may be used as a colony for a proliferation mass-production of the present animal.

Moreover, for the present animal, the trait of alopecia is inherited on a dominant gene, and a crossing of an individual whose "dec" allele has a genotype of dec/dec homo with an animal having a genotype of +/+ homo (normal gene is shown as +) provides individuals having a hetero (dec/+) genotype and exhibiting alopecia. Accordingly, for the mass-production of the present animals, a crossing of a "dec/dec" animal, either male or female, with a "+/+" animal can be used, and this method is very efficient.

Moreover, the use of in vitro fertilization may further improve the efficiency of the proliferation. In this case, for example, a lot of female animals of any strain such as C57BL or CH3 (genotype +/+) are crossed with an animal of the present invention having a genotype dec/dec, by an in vitro fertilization, and the resulting dec/+ embryo is transferred into the oviduct or the uterus of recipients of any strain, such as ICR or MCH. Since all of the resulting animals have a genotype dec/+, the onset of alopecia is guaranteed. It is possible to obtain a lot of new born animals from one animal of the present invention, by an in vitro fertilization.

Characteristics of the present animal

1) Progress of alopecia

Table 2 shows the progress of epilation with an elapse of time in 25 female mice and 24 male mice, observed until 30 weeks old. For female mice, no individuals start epilation until 3 weeks old, and at 10 weeks old 84% of individuals reached "±", but only 16% of individual reached "+". Thereafter, the ratio of individuals showing a "+" degree of epilation is gradually increased as the weeks elapse, and at 20 weeks old mice showing a "++" degree of epilation appear. The ratio of "±", "+", and "++" at 30 weeks old was 40%, 20%, and 40%, respectively.

On the other hand, for male mice, at 3 weeks old one individual had started epilation, and at 10 weeks old, 58% of the mice had a ± degree of epilation and 38% of the mice had a + degree of epilation. At 15 weeks old, the ratio of mice having a + degree of epilation reached the maximum, and thereafter decreased, and the ratio of mice having a ++ degree of epilation increased. At 30 weeks old, 38% of the mice had a ± degree of + epilation, 62% of the mice had a ++, but mice having a degree were not observed.

As seen from the above, it is considered that there is a difference in the progress of alopecia in males and in females. Namely, at 10 weeks old, 16% of the female mice had a + degree of epilation, but 38% of the male mice had a + degree of epilation; at 25 weeks old, a ratio of female mice having a ± degree of epilation was maximum (52%) and a ratio of male mice having a ++ degree of epilation was maximum (54%). Then, at 30 weeks old, considering the ratio of ±, +, and ++, it is recognized that the progress of alopecia is faster in male mice than in female mice.

TABLE 2

Ratio (%) of degrees (− to ++) of progress of alopecia at different age in growth

| Female | 3 | 5 | 10 | 15 | 20 | 25 | 30wks |
|---|---|---|---|---|---|---|---|
| − | 100 | 72 | 0 | 0 | 0 | 0 | 0 |
| ± | 0 | 12 | 84 | 56 | 52 | 52 | 40 |
| + | 0 | 16 | 16 | 44 | 28 | 12 | 20 |
| ++ | 0 | 0 | 0 | 0 | 20 | 36 | 40 | n = 25

| Male | 3 | 5 | 10 | 15 | 20 | 25 | 30wks |
|---|---|---|---|---|---|---|---|
| − | 96 | 79 | 0 | 0 | 0 | 0 | 0 |
| ± | 0 | 4 | 58 | 38 | 38 | 38 | 38 |

TABLE 2-continued

Ratio (%) of degrees (− to ++) of progress of alopecia at different age in growth

| + | 4 | 13 | 38 | 54 | 42 | 8 | 0 |
|---|---|---|---|---|---|---|---|
| ++ | 0 | 4 | 4 | 8 | 20 | 54 | 62 | n = 24

Tables 3 and 4 show average weeks at which alopecia of the present animals reached different degrees (±, +, or ++), as observed until 30 weeks old. The age at which ± mice (mice which exhibited a ± degree of epilation on 30 weeks old) started epilation was 7.0±1.6 weeks for females and 7.2±1.5 weeks for males, showing no difference between male and female. For ++ mice (mice which exhibited ++ degree of epilation at 30 weeks old), however, although the age at which epilation started was 6.0±0.9 weeks for females and 5.7±0.9 weeks for males, showing no difference between males and females, the age at which epilation reached a degree was 11.1±4.0 weeks for females and 8.9±2.9 weeks for males, showing a statistically significant difference between males and females. Since the age at which epilation reached to ++ degree was the same for both males and females, it is considered that the speed of progress from ± degree to + degree is faster in males than in females.

TABLE 3

Age at which epilation in female mice reaches a different degree

| Mice | Degree of progress of epilation | | |
|---|---|---|---|
| (n = ) | ± | + | ++ |
| ±(10) | 7.0 ± 1.6 | | |
| +(5) | 5.8 ± 0.4 | 26.2 ± 6.4 | |
| ++(10) | 6.0 ± 0.9 | 11.1 ± 4.1 | 20.9 ± 3.4 |

Mean ± SD(weeks old)

TABLE 4

Age at which epilation in male mice reaches a different degree

| Mice | Degree of process of epilation | | |
|---|---|---|---|
| (n =) | ± | + | ++ |
| ±(9) | 7.2 ± 1.5 | | |
| +(0) | — | — | |
| ++(15) | 5.7 ± 0.9 | 8.9 ± 2.9 | 20.1 ± 5.1 |

Mean ± SD(weeks old)

The normal hair of mouse is classified as Type A (Monotrich), Type B (Awl), Type C (Auchene) and Type D (Zig zag) (M. M. Dickie and G. W. Wooly, Fuzzy mice, J. Hered. 41,193–196(1950)), and as the hair of the present animal belongs to Type A, B or C, it is normal.

2) Growth curve

FIGS. 1 and 2 show growth curves of the present animals and normal animals, as a reference. Alopecia female mice are often heavier in weight than normal female mice. Namely, although a difference in body weight is not observed from weaning to 6 weeks old, thereafter a statistically significant difference in body weight is found. Since the difference is not significant at 20 weeks old, it is shown that, after 6 weeks of age, the rate of increase of body weight is different. For male mice, although a difference is not recognized between alopecia mice and normal mice, thereafter the normal mice become significantly heavier than alopecia mice after 20 weeks of age.

3) Histological observation of the dorsal skin

The epidermis of the present mouse is thicker than that of a normal mouse, but an abnormal progress of keratinization is not observed. In some parts the epidermis invaginates into the corium, the invagination becomes remarkable with aging, and the granular layer and prickle cell layer grow. Although melanin pigment is not present in the epidermal basal layer of normal mouse, in the parts of the basal layer and prickle cell layer of the present mouse where the epidermis invaginates into the corium, melanin pigment is observed. This is one of the major characteristics of the present animal.

The hair follicles of the present mouse are disseminated and irregularly distributed, and in some parts degeneration of the hair bulb is observed. The number of sebaceous glands decreases depending on the progress of epilation. The connective tissue in the corium is solid, an increase of the number of monocytes is observed around the hair follicle or disseminated, and the deposition of melanin pigment is observed in some parts.

4) Effect of UV radiation on the dorsal skin

UV in the A region (UV-A; 320–400 nm) was radiated onto the back of the present mice when 3 months old and 9 months old, at an intensity of 1 to 2 $J/cm^2$, and after 2 weeks and 4 weeks from the radiation, the skin was examined histopathologically observed and the following characteristic findings obtained.

After 2 weeks from the UV radiation, for a 3 months old mouse, the melanine pigment was clearly increased not only in the epidermal basal layer but also in the horny layer, although the melanine pigment was not increased in the corium connective tissue. After 4 weeks from the radiation only disseminated melanine pigment was observed in the epidermal basal layer, but this was different from that of non-radiated portion.

On the other hand, after 2 weeks from the UV radiation for a 9 months old mouse, although a small amount of melanine pigment was observed in the epidermal basal layer of a large amount of melanine pigment was present in the corium connective tissue. After 4 weeks from the radiation, this tendency became more remarkable. Namely, very little deposition of melanine pigment was found in the epidermal basal layer and melanine pigment was predominantly observed in the corium connective tissue. Therefore, the UV radiation onto the dorsal skin of the present mouse induces a deposition of melanine pigment in the epidermal basal layer of a 3 months old mouse and in the corium connective tissue of a 9 months old mouse.

5) Other properties

In the present mouse at 12 to 13 weeks old, regardless of the degree of progress of alopecia, a projection of the eyeballs is observed in all suffering individuals. A drying of the cornea occurs, due to an insufficient closing of the eyelids caused by the projection of the eyeballs, resulting in whitening of the surface of the eyeballs. Note, a projection of the eyeballs is not observed in normal individuals.

The present animal has the following advantages.

1) The present animal inherits the trait of alopecia by a dominant gene, and as the reproduction efficiency rate is high, a mass production of the present mouse is possible. Therefore, the present animal can be used for carrying out efficient experiments and for stabilizing the supply of experimental animals.

2) The progress of alopecia is relatively slow, and therefore the present animal is promising an animal model for human disease or experimental animals which provide valuable information on the development of prophylactic methods or treating of human alopecia, and research into clarifying the onset mechanism.

3) The response of melanocytes to UV radiation changes with aging.

Also, the deposition pattern of melanine pigment in the epidermis and the corium in the dorsal skin of the present animal changes with aging. Namely, the deposition of melanine pigment moves from the epidermal basal layer to the corium connective tissue. Accordingly, the present animal is promising as a human photodermatosis model, sunburn model (deposition of melanine in the epidermis) and liverspot/ephelis model (deposition of melanine in the corium).

4) The numbers of hairs and hair follicles are small.

This property can be used for testing drugs whose transdermal absorption varies depending on the number of follicles.

EXAMPLES

Next, the present invention is explained in more detail with reference to Examples.

1) Production of the present animals by in vitro fertilization and freezing of embryos In vitro fertilization was carried out using 3 mature males of the present invention and 28 mature C57BL/6J female mice, and the production of the present animals and the freeze-storing of embryos were carried out as follows.

Female mice were subjected to super ovulation treatment by administering 5 units each of PMSG (pregnant mare serum gonadotropin) and hCG (human chorionic gonadotropin) at 48 hour interval. And 16 hours after the hCG administration, the treated animals were subjected to euthanasia by cervical dislocation, and the oviductus was removed. The removed oviductus was put on a filter paper to remove the blood, and put into liquid paraffin oil (Merck) in a plastic petri dish (35×10 mm, Falcon).

Next the ampulla of the oviduct was broken with anatomical needles, and oocytes surrounded by cumulus cells were introduced into 0.4 ml of mouse in vitro fertilization medium (Y. Toyoda et al., Studies on fertilization of mouse eggs in vitro. I, In vitro fertilization of egg by fresh epididymal sperm, Jpn. J. Anjm. Reprod, 16, 147–151(1971)). Note, to obtain sperm, a male mouse was subjected to euthanasia as described above for the female mouse, the cauda epididymus was removed, and a part thereof containing sperm and having a white color was cut into sections with ophthalmological scissors. The leaked mass of sperm was picked up with a dissecting needle, and immediately introduced into 0.2 ml of a mouse in vitro fertilization medium.

Next, after a preincubation of 2 hours, the sperm suspension was added to a medium containing oocytes at a concentration of 150 sperms/µl. A judgment of the fertilization was carried out by a confirmation of both the male and female pronucleus and extrusion of the second polar body 6 hours after the insemination. The embryo tranfer was carried out by injecting eggs in a pronucleus stage 7 to 8 hours after insemination to an oviductum of MCH or ICR pseudopregnant recipient at the day of vaginal plug detection.

In recipient mice, anesthetized by an intraperitoneal administration of sodium pentobarbital (Nembutal; Abott Laboratories) there was made a small transverse incision with the dissecting scissors, about 1 cm to the left or the right of the spinal cord, at the level of the last rib, and the ovary, oviduct and uterine horn were pulled out. Next, a part of ovarian bursa was cut and 7 eggs per an oviduct of ova were introduced into fimbria with a small volume of medium, using a glass capillary pipette connected to a mouthpiece. After the operation, each recipient female mouse was kept separate, and allowed to carry out delivery and nursing. Weaning was carried out at 3 weeks old.

The result of in vitro fertilization of DEC mouse is shown in Table 5, and the result of the embryo transfer is shown in Table 6.

TABLE 5

Result of in vitro fertiliaztion of DEC mouse

| Exp. No. | Male (N =) | Female (N =) | | Number of Fertilized Ova/Number of Ovulated Ova(%) |
|---|---|---|---|---|
| 1 | DEC(F3-9) | (1) C57BL/6J | (6) | 141/164(86.0) |
| 2 | DEC(F3-11) | (1) C57BL/6J | (5) | 91/114(79.8) |
| 3 | DEC(F4-6) | (1) C57BL/6J | (17) | 268/375(71.5) |
| Total | | (3) | (28) | 500/653(76.6) |

TABLE 6

Result of embryo transfer of DEC mouse

| Number of transferred ova | Number of pregnant females/number of females (%) | Number of animals born (%) |
|---|---|---|
| 306 | 23/24 (95.8) | 148 (48.4) |

Ova in pronucleus stage, not used for embryo tranfer, were cultured in a mouse embryo culture medium supplemented with 100 μM EDTA (M. Hoshi and Y. Toyoda, Effect of EDTA on the preimplanation development of mouse embryos fertilized in vitro Jpn. J. Zootech Sci. 56, 931–937 (1985)), and at about 54 hours after insemination embryos developed to the four cell stage to morula were frozen by a vitrification method (W. F. Rall and G. M. Fahy, Ice-free cryopreservation of mouse embryo at −196° C. by vitrification, Nature 313, 573–575 (1985)).

Then 500 fertilized ova were obtained from 3 male mice, corresponding to 167 ova/a mouse (Table 5), and an embryo tranfer of 306 fertilized ova provided 148 animals born, corresponding to 80.8 animals born/a male mouse (Table 6). Since this figure depends on the number of ovum donor female mice, a larger number of mice can be produced by increasing the number of female mice.

2) Measurement of hair follicles and density of hair

The skin of the present animal and of a normal animal was peeled under anesthesia with sodium pentobarbital (Nenbutal; Abott Laboratories), and after fixing, the skin was observed under a stereomicroscope using incident light or penetrating light. After taking a photograph thereof, the densities of the hair and the hair follicles were calculated. Note, where the density of hair is too high to be observed, the hair was cut with a pair of electric hair clippers for small animals or for human, and thereafter, the skin was fixed.

The degree of epilation was expressed by "++", "+", and "±", from the density of hair on the dorsal surface. Namely, in an observation by the naked eye, a "++" degree is a condition of entire epilation (hairless) except for the face; a "+" degree is a condition where, although the presence of hair is recognized by the naked eye, the hair does not entirely cover the skin and the surface of the skin can be seen; and a "±" degree is that wherein, although hair entirely covers the skin, it is distinguished from "normal" in that the distribution of hair is rough, and the gloss is apparently lost.

As shown by the results appearing in Table 7. "++", "+", and "±" mice had $57.5 \pm 50.5/cm^2$, $252.5 \pm 136.8/cm^2$, and $4700 \pm 1003/cm$ hairs respectively. Note a normal individual had $7750 \pm 1255$ hairs. A normal individual and a "±" individual had more than one hair per one hair follicle, and "+" and "++" individuals had only one hair per one hair follicle.

TABLE 7

Density of hair and hair follicles

| | Number of hairs | Number of hair follicles |
|---|---|---|
| normal | 7750 ± 1255 | 3880 ± 630 |
| ± | 4700 ± 1003 | 1880 ± 400 |
| + | 253 ± 137 | 253 ± 137 |
| ++ | 57.5 ± 50.5 | 57.5 ± 50.5 |

Mean ± SD (per $cm^2$)

3) Effect of UV radiation onto dorsal skin on deposition of melanine pigment

First, 500 ppm 8-methoxy psoralen was coated on the dorsal skin of the present mice when 3 and 6 months old at an amount of 5 μl/$cm^2$, and after 30 minutes, an A region UV (UV-A; 320–400 nm) was radiated onto the skin at a dose of 0 25 10 J/$cm^2$, using a medical UV radiation apparatus (TOREX; M-DMR-80, Tohshiba Iryo K.K.). Four days after the radiation minimum erythema dose (MED) was determined. Next, 2 to 4 MED of UV was radiated, and 4 weeks after the radiation, an observation by the naked eye was carried out, and 2 weeks and 4 weeks after the radiation, a histopathological examination was carried out.

Prior to the radiation, the entire body of a test animal, except for a part to be radiated (1×1 cm–1.5×1.5 cm), was covered with aluminum foil, and the radiation was carried out under anesthesia with sodium pentobarbital (Nenbutal; Abott Laboratories). Note the UV dose was measured by a UV photo meter (UVR-305/365.D(II); TOPCON CO.).

The minimum erythema dose (MED) of A region UV for the present animal was 0.5 J/$cm^2$. For an individual receiving a dose which is the same as or more than 2 J/$cm^2$, a change of the skin color to white, red or black was observed by the third day, after radiation. Doses of 0.5 J/$cm^2$ and 1 J/$cm^2$ caused a whitening of the skin at the fourth day, but a dose of 0.25 J/$cm^2$ did not cause a change of the skin that could be detected by the naked eye during the observation period.

After the fourth day, for a 3 months old mouse and 6 months old mouse, a sore or abrasion of the skin was observed at a dose which was the same as or more than 5 J/$cm^2$, but for a 6 months old mouse, abrasion of the skin was observed at a dose of 2 J/$cm^2$. Three weeks after the radiation at a 0.5 J/$cm^2$, the black colored of the skin disappeared, but for a 1 J/$cm^2$ radiation, although the black color faded, the color did not completely disappear. The response to the same radiation dose was clearly different for 3 months old mouse and for a 6 months old mouse. Namely, sores or an abrasion of the skin were clearly more severe in a 6 months old mouse than in a 3 months old mouse, revealing that the effect of UV radiation becomes greater as the aging of the mouse progresses.

Histopathological findings were made as follows. For a 3 months old mouse, 2 weeks after a radiation of 1 J/$cm^2$, melanine pigment was present not only in the epidermal basal layer but also in the horny substance layer, but was not observed in the corium connective tissue. At a dose of 2 J/cm$^2$, the deposition of melanine pigment was observed as same degree as a dose of 1 J/cm$^2$, but was found more extensively. Four weeks after the radiation, only disseminated melanine pigment was observed in the epidermal basal layer, but this was different from that of non-radiated portion. Conversely, for a 6 months old mouse, 2 weeks after the radiation of 1 or 2 J/cm$^2$, although a small amount of melanine pigment was observed in the epidermal basal layer, a large amount of melanine pigment was present in the corium connective tissue. Moreover, the progress of keratinization, an increase of keratohyaline granules, and a hypertrophy of the epidermis were observed. At a dose of 2 J/cm$^2$, some individuals were observed to have an ulcerated skin, and after 4 weeks, there was very little deposition of melanine in the epidermal basal layer, and melanine was observed predominantly in the corium connective tissue. Namely, a UV radiation onto the dorsal skin caused a deposition of melanine pigment in the epidermal basal layer in a 3 months old mouse, and in the corium connective tissue in a 6 months old mouse.

We claim:

1. The DEC strain of mouse which inherits by a dominant gene the following properties:

(1) the mouse suffers from alopecia when 6 to 7 weeks old;

(2) the alopecia gradually progresses, and over about 5 months a hairless condition is reached, as observed by the naked eye;

(3) at 12 to 13 weeks old, the eyeballs of all suffering mice project;

(4) melanin pigment is deposited in the epidermal base layer and corium connective tissue; and (5) increased melanin pigment is deposited in response to UV radiation.

2. The DEC strain of claim 1 which is deposited mouse strain ATCC 72004.

* * * * *